United States Patent [19]

Mikkelsen

[11] Patent Number: Plant 5,254

[45] Date of Patent: Jul. 3, 1984

[54] KALANCHOE PLANT NAMED ROYALTY

[75] Inventor: James C. Mikkelsen, Ashtabula, Ohio

[73] Assignee: Mikkelsens, Inc., Ashtabula, Ohio

[21] Appl. No.: 422,150

[22] Filed: Sep. 23, 1982

[51] Int. Cl.[3] ..... A01H 5/00

[52] U.S. Cl. ..... Plt./68

[58] Field of Search ..... Plt./68

*Primary Examiner*—Bagwill Robert E.

*Attorney, Agent, or Firm*—Schwartz, Jeffery, Schwaab, Mack, Blumenthal & Koch

[57] ABSTRACT

A kalanchoe plant named Royalty, characterized by its excellent keeping quality, free branching and vigorous growth habits, well clustered, rose-red flowers, high floriferousness, and its adaptability to various pot sizes and to growth regulators.

1 Drawing Figure

The present invention relates to a new and distinct cultivar of kalanchoe plant, botanically known as kalanchoe, and referred to by the cultivar name Royalty. Royalty was discovered by me as a mutation of kalanchoe cultivar Sensation, disclosed in U.S. Plant Pat. No. 4,727, within several flowering crops of the parent cultivar in 10 cm. plastic pots in Ashtabula, Ohio early in 1981. Except for flower color the mutation is very comparable to the parent cultivar Sensation in all details. Asexual reproduction by stem cuttings has shown that the unique features of this new kalanchoe are stabilized and are reproduced true to type in successive propagations.

The following characteristics distinguish the new kalanchoe from both its parent cultivars and other cultivated kalanchoes of this type known and used in the floriculture industry:

1. In comparison to Sensation, the flower color is best described as a rose red.
2. In the illustration of Sensation in U.S. Plant Pat. No. 4,727, the individual cymes appear to be highly separated when compared to the present illustration of Royalty. The technology of applying growth regulators has been greatly improved since Mar. 26, 1980, so that the inflorescence of Royalty has been made more compact with applications of B9 during flower initiation.
3. Royalty has excellent keeping quality of the foliage and the flowers, both in the greenhouse and in the home.
4. Proper scheduling makes the new cultivar suitable for production in 10 to 15 cm. pots.
5. After flower initiation, the growth of the terminal shoot slows down, resulting in approximately the same length of the terminal and side peduncles at flowering time, adding to the total flower placement.
6. During flower initiation, plants must be treated with B9 in all seasons to reduce peduncle elongation.
7. Flowering time is 10 weeks in summer to 14 weeks in winter after start of short days.
8. Well clustered rose-red flowers, and highly floriferous.
9. Freely branching with or without pinching.
10. Plant growth is vigorous, as in Sensation.
11. Flower size the same as in Sensation.
12. Foliage is nearly the same size and shape as Sensation, but the leaf margin is more distinctly crenated.

The accompanying colored photograph taken April, 1982, illustrates in perspective view the overall appearance of Royalty grown in 10 cm. plastic pots and showing the colors as true as it is reasonably possible to obtain in a colored reproduction of this type.

The following is a detailed description of my new kalanchoe cultivar based on plants produced under commercial practices in the greenhouses of Mikkelsens, Inc. at Ashtabula, Ohio. Color references are made to The Royal Horticultural Society Colour Chart except where general terms of ordinary dictionary significance are used.

PARENTAGE

A color mutation of the kalanchoe cultivar Sensation, disclosed in U.S. Plant Pat. No. 4,727.

PROPAGATION (A) Type of cutting: Short tip cutting, with stems up to 2 cm. long.

(B) Time to root: 10 Days at 21° C. summer, 14 days at 21° C. winter.

(C) Rooting habit: Many very fine roots, fibrous.

PLANT DESCRIPTION (A) Form: Short, compact, upright growth. Growing and scheduling practices can produce a small plant in a 10 cm. pot up to a larger plant in a 15 cm. pot.

(B) Habit of growth: Rate of growth moderate for this type of plant. Generally, shoots are formed at every node.

(C) Foliage description: Leaves simple, opposite. Frequently, leaves are asymmetrical, with a slight tendency to bend or twist.

*Size.*—Average full grown leaf 130 mm. long × 80 mm. wide. Full grown leaves have petioles up to 30 mm. long, young leaves have short petioles.

*Shape.*—Ovate to elliptic, apex obtuse, base attenuate.

*Texture.*—Glabrous, coriaceous, succulent.

*Margin.*—Sinuate to crenate.

*Color.*—Young foliage, top side green 137B, under side green 138A. Mature foliage, top side darker than green 137A to yellow green 147A, under side green 137A–B.

FLOWERING DESCRIPTION (A) Flowering habits: Inflorescence of each shoot is formed by dichotomous branching, starting with opening of terminal flower of main axis, followed by terminal flowers of the side branches, continuing with subsequent development of branches in the inflorescence. Opening of new buds will continue for two months or more. Individual flowers last two weeks or more after opening.

(B) Natural flowering season: Late January. Flowering time under controlled daylength at 20° C. in summer is 10 weeks; in winter 14 weeks. Flowering time depends on temperature, light intensity and other growing conditions.

(C) Flower bud description: Elliptical to oblong, up to 8 mm. long, developing to tubular as flower petals mature, sheathed with four green sepals. Corolla at maturity, 8 mm. long.

(D) Flowers borne: Compound dichasial cyme on strong peduncles. Primary peduncle is 5 mm. in diameter, with peduncle length depending on growing conditions and B9 application; pedicels up to 8 mm. long.

(E) Quantity of flowers. Highly floriferous. Main axis and side shoots have 100 or more flowers.

(F) Petals:

(1) *Shape.*—Nearly round with top slightly cuspidate.

(2) *Color.*—Top side when opening, red 51-A, fading to red 54B to 52 b, under side red 52B-C.

(3) *Number of petals.*—Four (4), united in corolla, salverform; petals 6 mm. in diameter, and total flower diameter 16 mm.

(G) Reproductive organs:

(1) *Stamens.*—Eight (8) in number. (a) Anther shape: Flat, elliptical, color light brown; frequently, anthers are degenerated, with dark brown color. (b) Filament color: Light green. (c) Pollen color: Yellow.

(2) *Pistels.*—(a) Stigma shape; Flat, crystalline, color greenish white. (b) Style color: Light green. (c) Ovary: 4 Celled, 6 mm. long, color green 143A.

DISEASE RESISTANCE

No diseases or adverse physiological problems observed to date. Cultivar is highly resistant to mildew.

I claim:

1. A new and distinct cultivar of kalanchoe plant, known by the cultivar name Royalty, as described and illustrated, and particularly characterized by its excellent keeping quality, free branching habit, well clustered, rose-red flowers, highly floriferous and vigorous habit, and adaptability to various pot sizes and to growth regulators.

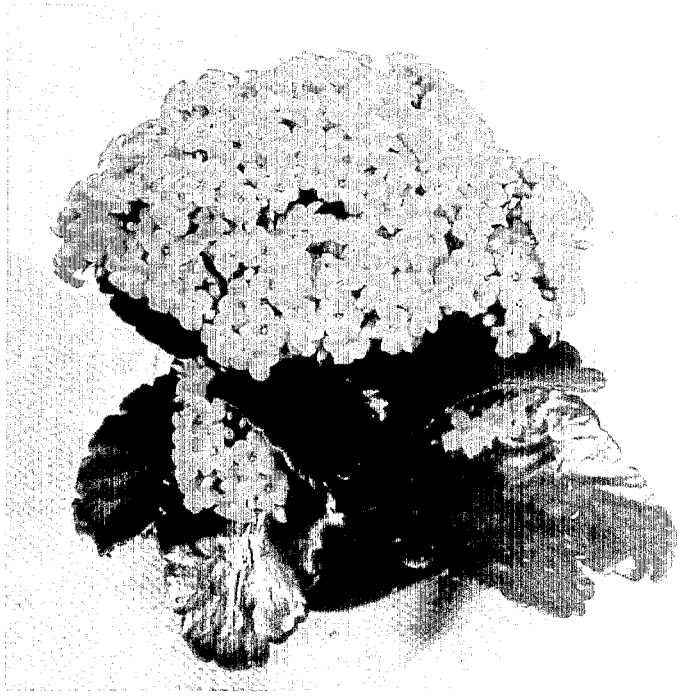

* * * * *